United States Patent [19]

Schinazi et al.

[11] Patent Number: 5,905,070

[45] Date of Patent: May 18, 1999

[54] [5—CABOXAMIDO OR 5—FLUORO]—[2', 3'—UNSATURATED OR 3'—MODIFIED]—PYRIMIDINE NUCLEOSIDES

[75] Inventors: Raymond F. Schinazi, Decatur; Dennis C. Liotta, McDonough, both of Ga.

[73] Assignee: Emory University, Atlanta, Ga.

[21] Appl. No.: 09/001,084

[22] Filed: Dec. 30, 1997

Related U.S. Application Data

[63] Continuation of application No. 08/379,276, Jan. 27, 1995, Pat. No. 5,703,058.

[51] Int. Cl.$^6$ .......................... A61K 31/70; A61K 38/00; C07H 19/06

[52] U.S. Cl. .................................. 514/49; 514/2; 514/45; 514/50; 514/269; 514/274; 536/26.23; 536/26.26; 536/26.8; 536/28.2; 536/28.5; 536/28.52; 536/28.53; 536/28.55; 544/310; 544/317

[58] Field of Search ................... 514/2, 45, 49, 514/50, 269, 274; 536/28.5, 28.52, 28.53, 28.55, 28.2, 26.8, 26.23, 26.26; 544/370, 317

[56] References Cited

U.S. PATENT DOCUMENTS

| | | | |
|---|---|---|---|
| 3,116,282 | 12/1963 | Hunter | 536/28.52 |
| 5,210,085 | 5/1993 | Liotts et al. | 514/274 |
| 5,233,041 | 8/1993 | Bray et al. | 544/276 |
| 5,241,069 | 8/1993 | Vince et al. | 544/277 |
| 5,329,008 | 7/1994 | Partridge et al. | 54/276 |
| 5,521,161 | 5/1996 | Malley et al. | 514/45 |
| 5,561,120 | 10/1996 | Lin et al. | 514/49 |
| 5,567,688 | 10/1996 | Chu et al. | 514/46 |
| 5,703,058 | 12/1997 | Schinazi et al. | 514/45 |

FOREIGN PATENT DOCUMENTS

| | | |
|---|---|---|
| 0409227 | 1/1991 | European Pat. Off. . |
| 7109221 | 4/1995 | Japan . |
| 8901258 | 12/1990 | Netherlands . |
| 9214743 | 9/1992 | WIPO . |
| 9409793 | 5/1993 | WIPO . |
| 9323021 | 11/1993 | WIPO . |
| 9414831 | 7/1994 | WIPO . |
| 9427590 | 12/1994 | WIPO . |

OTHER PUBLICATIONS

Abobo et al., "Pharmacokinetics of 2', 3'–Dideoxy–5–fluoro–3'–thiacytidine in Rats," *J. Pharmaceutical Sciences*, 83(1), 96–99(1994).

Aerschot et al., "Synthesis and Anti–HIV Evaluation of 2', 3'–Dideoxy–5–chloropyrimidine Analogues: Reduced Toxicity of 5–Chlorinated 2', 3'–Dideoxynucleosides," *J. Medicinal Chem.*, 33(6), 1833–1839 (1990).

Balzarini et al.(I), "5'–Chloro–substituted Derivatives of 2', 3'–Didehydro–2', 3'–dideoxyuridine, 3–Fluoro–2', 3'–dideoxyuridine and 3'–Azido–2', 3'–dideoxyuridine as Anti–HIV Agents," *Biochem. Pharmacology*, 38(6), 869–874 (1989).

Balzarini et al. (II), "2', 3'–Didehydro–2', 3'–dideoxy–5–chlorocytidine Is A Selective Anti–Retrovirus Agent," *Biochem. Biophys. Res. Comm.*, 164(3), 1190–1197 (1989).

Condreay et al., "Evaluation of the Potent Anti–Hepatitis B Virus Agent (–) cis–5–Fluoro–1–[2–(Hydroxymethyl)–1, 3–Oxathiolan–5–yl] Cytosine in a Novel In Vivo Model," *Antimicrobial Agents and Chemotherapy*, 38(3), 616–619 (1994).

Feorino et al., "Prevention of Activation of HIV–1 by Antiviral Agents in OM–10.1 Cells," *Antiviral Agents & Chemotherapy*, 4(1), 55–63 (1993).

Frick et al. (I), "Pharmacokinetics, Oral Bioavailability, and Metabolic Disposition in Rats of (–) cis–5–Fluoro–1–[2–(Hydroxymethyl)–1, 3–Oxathiolan–5–yl] Cytosine, a Nucleoside Analog Active Against Human Immunodeficiency Virus and Hepatitis B Virus," *Antimicrobial Agents and Chemotherapy*, 37(11), 2285–2292 (1993).

Frick et al. (II), "Pharmacokinetics, Oral Bioavailability, and Metabolic Disposition in Mice and Cynomolgus Monkeys of (2'R, 5'S–)–cis–5–Fluoro–1–[2–(Hydroxymethyl)–1, 3–Oxathiolan–5–yl] Cytosine, an Agent Active Against Human Immunodeficiency Virus and Hepatitis B Virus," *Antimicrobial Agents and Chemotherapy*, 38(12), 2722–2729 (1994).

Gu et al., "Identification of a Mutation at Codon 65 in the IKKK Motif of Reverse Transcriptase That Encodes Human Immunodeficiency Virus Resistant to 2', 3'–Dideoxycytidine and 2', 3'–Dideoxy–3'–Thiacytidine," *Antimicrobial Agents and Chemotherapy*, 38(2), 275–281 (1994).

Hoong et al., "Enzyme–Mediated Enantioselective Preparation of Pure Enantiomers of the Antiviral Agent 2', 3'–Dideoxy–5–fluoro–3'–thiacytidine (FTC) and Related Compounds," *J. Organic Chem.*, 57(21), 5563–5565 (1992).

Jansen et al., "High–Capacity In Vitro Assessment of Anti–Hepatitis B Virus Compound Selectivity by a Virion–Specific Polymerase Chain Reaction Assay," *Antimicrobial Agents and Chemotherapy*, 37(3), 441–447 (1993).

(List continued on next page.)

Primary Examiner—Marian C. Knode
Assistant Examiner—L. Eric Cane
Attorney, Agent, or Firm—Sherry M. Knowles; Jacqueline Haley; King & Spalding

[57] ABSTRACT

A method and composition for the treatment of HIV and HBV infections in humans and other host animals is disclosed that includes the administration of an effective amount of a [5-carboxamido or 5-fluoro]-2',3'-dideoxy-2', 3'-didehydro-pyrimidine nucleoside or a [5-carboxamido or 5-fluoro]-3'-modified-pyrimidine nucleoside, or a mixture or a pharmaceutically acceptable derivative thereof, including a 5' or $N^4$ alkylated or acylated derivative, or a pharmaceutically acceptable salt thereof, in a pharmaceutically acceptable carrier.

19 Claims, No Drawings

OTHER PUBLICATIONS

Jeong et al., "Structure–Activity Relationships of β–D–(2S, 5R)– and α–D–(2S, 5R)—1,3–Oxathiolanyl Nucleosides as Potential Anti–HIV Agents," *J. Medicinal Chem.*, 36(18), 2627–2638 (1993).

Kim et al., "Asymmetric Synthesis of 1,3–Dioxolane–Pyrimidine Nucleosides and heir Anti–HIV Activity," *J. Medicinal Chem.*, 35(11), 1987–1995 (1992).

Mathez et al., "Infectious Amplification of Wild–Type Human Immunodeficiency Virus from Patients' Lymphocytes and Modulation by Reverse Transcriptase Inhibitors In Vitro," *Antimicrobial Agents and Chemotherapy*, 37(10), 2206–2211 (1993).

Mansour et al. (I), "Structure–Activity Relationships Among a New Class of Antiviral Heterosubstituted 2', 3'–Dideoxynucleoside Analogues," *Nucleosides & Nucleotides*, 14(3–5), 627–635 (1995).

Mansour et al. (II), "Anti–Human Immunodeficiency Virus and Anti–Hepatitis–B Virus Activities and Toxicities of the Enantiomers of 2'–Deoxy–3'–oxa–4'–thiocytidine and Their 5–Fluoro Analogues in Vitro," *J. Medicinal Chem.*, 38(1), 1–4 (1995).

Paff et al., "Intracellular Metabolism of (–)– and (+)–cis–5–Fluoro–1–[2–(Hydroxymethyl)–1, 3–Oxathiolan–5–yl] Cytosine in HepG2 Derivative 2.2.15 (Subclone P5A) Cells," *Antimicrobial Agents and Chemotherapy*, 38(6) 1230–1238 (1994).

Roey et al., "Absolute Configuration of the Antiviral Agent (–)–cis–5–Fluoro–1–[2–(Hydroxymethyl)–1, 3–Oxathiolan–5–yl] Cytosine," *Antiviral Agents and Chemotherapy*, 4(6), 369–375 (1993).

Shewach et al., "Affinity of the Antiviral Enantiomers of Oxathiolane Cytosine Nucleosides for Human 2'–Deoxycytidine Kinase," *Biochem. Pharmacology*, 45(7), 1540–1543 (1993).

Schinazi et al. (I), "Antiviral Drug Resistance Mutations in Human Immunodeficiency Virus Type 1 Reverse Transcriptase Occur in Specific RNA Structural Regions," *Antimicrobial Agents and Chemotherapy*, 38(2), 268–274 (1994).

Schinazi et al., "Characterization of Human Immunodeficiency Viruses Resistant to Oxathiolane–Cytosine Nucleosides," *Antimicrobial Agents and Chemotherapy*, 37(4), 875–881 (1993).

Tisdale et al., "Rapid In Vitro Selection of Human Immunodeficiency Virus Type 1 Resistant to 3'–Thiacytidine Inhibitors Due to a Mutation in the YMDD Region of Reverse Transcriptase," *Proc. Nat. Acad. Sci. USA*, 90, 5653–5656 (Jun. 1993).

Van Draanen et al., "Influence of Stereochemistry on Antiviral Activities and Resistance Profiles of Dideoxycytidine Nucleosides," *Antimicrobial Agents and Chemotherapy*, 38(4), 868–871 (1994).

Biron et al., "Anti–HIV Activity of the Combination of Didanosine and Hydroxyurea in HIV–1 Infected Individuals," *J. AIDS and Human Retrovirology*, 10(1), 36–40 (Aug. 1995).

Lori et al., "Hydroxyurea as an Inhibitor of Human Immunodeficiency Virus–Type 1 Replication," *Science*, 266, 801–805 (Nov. 4, 1994).

Vince et al., "Resolution of Racemic Carbovir and Selective Inhibition of Human Immunodeficiency Virus by the (–) Enantiomer," *Biochemical and Biophysical Res. Comm.*, 168(3), 912–915 (May 16, 1990).

Parker et al., "Mechanism of Inhibition of Human Immunodeficiency Virus Type 1 Reverse Transcriptase and Human DNA Polymerases α, β, and γ by the 5'–Triphosphates of Carbovir, 3'–Azido–3'–deoxythymidine, 2',3'–Dideoxyguanosine, and 3'–Deoxythymidine," *J. Biological Chem.*, 208(3), 1754–1762 (Jan. 25, 1991).

[5— CABOXAMIDO OR 5— FLUORO]— [2', 3'— UNSATURATED OR 3'— MODIFIED]— PYRIMIDINE NUCLEOSIDES

This application is a continuation of U.S. Ser. No. 08/379,276, filed on Jan. 27, 1995, now U.S. Pat. No. 5,703,058.

BACKGROUND OF THE INVENTION

This invention is in the area of biologically active nucleosides, and specifically includes antiviral compositions that include a [5-carboxamido or 5-fluoro]-2',3'-dideoxy-2', 3'-didehydro-pyrimidine nucleoside or [5-carboxamido or 5-fluoro]-3'-modified-pyrimidine nucleoside, or its physiologically acceptable derivative, or physiologically acceptable salt.

In 1981, acquired immune deficiency syndrome (AIDS) was identified as a disease that severely compromises the human immune system, and that almost without exception leads to death. In 1983, the etiological cause of AIDS was determined to be the human immunodeficiency virus (HIV). The World Health Organization estimates that currently 13 million people worldwide are infected with HIV and that forty million people will be infected by the year 2000. Each day approximately 5,000 people are newly infected.

In 1985, it was reported that the synthetic nucleoside 3'-azido-3'-deoxythymidine (AZT) inhibits the replication of human immunodeficiency virus. Since then, a number of other synthetic nucleosides, including 2',3'-dideoxyinosine (DDI), 2',3'-dideoxycytidine (DDC), and 2',3'-dideoxy-2',3'-didehydrothymidine (D4T), have been proven to be effective against HIV. After cellular phosphorylation to the 5'-triphosphate by cellular kinases, these synthetic nucleosides are incorporated into a growing strand of viral DNA, causing chain termination due to the absence of the 3'-hydroxyl group. They can also inhibit the viral enxyme reverse transcriptase.

The success of various synthetic nucleosides in inhibiting the replication of HIV in vivo or in vitro has led a number of researchers to design and test nucleosides that substitute a heteroatom for the carbon atom at the 3'-position of the nucleoside. Norbeck, et al., disclosed that (±)-1 -[(2β,4β)-2-(hydroxymethyl)-4-dioxolanyl]thymine (referred to as (±)-dioxolane-T) exhibits a modest activity against HIV ($EC_{50}$ of 20 μM in ATH8 cells), and is not toxic to uninfected control cells at a concentration of 200 μM. *Tetrahedron Letters* 30 (46), 6246, (1989). European Patent Application Publication No. 0 337 713 and U.S. Pat. No. 5,041,449, assigned to IAF BioChem International, Inc., disclose that racemic 2-substituted-4-substituted-1,3-dioxolanes exhibit antiviral activity.

U.S. Pat. No. 5,047,407 and European Patent Application Publication No. 0 382 526, also assigned to IAF Biochem International, Inc. disclose a number of racemic 2-substituted-5-substituted-1,3-oxathiolane nucleosides with antiviral activity, and specifically report that the racemic mixture (about the C4'-position) of the C1'-β isomer of 2-hydroxymethyl-5-(cytosin-1-yl)-1,3-oxathiolane (referred to below as (±)-BCH-189) has approximately the same activity against HIV as AZT, and no cellular toxicity at the tested levels. (±)-BCH-189 has also been found to inhibit the replication of AZT-resistant HIV isolates in vitro from patients who have been treated with AZT for longer than 36 weeks. The (−)-enantiomer of the β-isomer of BCH-189, known as 3TC, which is highly potent against HIV and exhibits little toxicity, is in the final stages of clinical review for the treatment of HIV.

It has also been disclosed that (−)-cis-2-hydroxymethyl-5-(5-fluorocytosin-1-yl)-1,3-oxathiolane ("FTC") has potent HIV activity. Schinazi, et al., "Selective Inhibition of Human Immunodeficiency Viruses by Racemates and Enantiomers of cis-5-Fluoro-1-[2-(Hydroxymethyl)-1,3-Oxathiolane-5-yl]Cytosine" *Antimicrobial Agents and Chemotherapy,* November 1992, page 2423–2431;

Another virus that causes a serious human health problem is the hepatitis B virus (referred to below as "HBV"). HBV is second only to tobacco as a cause of human cancer. The mechanism by which HBV induces cancer is unknown, although it is postulated that it may directly trigger tumor development, or indirectly trigger tumor development through chronic inflammation, cirrhosis, and cell regeneration associated with the infection.

After a two to six month incubation period in which the host is unaware of the infection, HBV infection can lead to acute hepatitis and liver damage, that causes abdominal pain, jaundice, and elevated blood levels of certain enzymes. HBV can cause fulminant hepatitis, a rapidly progressive, often fatal form of the disease in which massive sections of the liver are destroyed.

Patients typically recover from acute hepatitis. In some patients, however, high levels of viral antigen persist in the blood for an extended, or indefinite, period, causing a chronic infection. Chronic infections can lead to chronic persistent hepatitis. Patients infected with chronic persistent HBV are most common in developing countries. By mid-1991, there were approximately 225 million chronic carriers of HBV in Asia alone, and worldwide, almost 300 million carriers. Chronic persistent hepatitis can cause fatigue, cirrhosis of the liver, and hepatocellular carcinoma, a primary liver cancer.

In western industrialized countries, high risk groups for HBV infection include those in contact with HBV carriers or their blood samples. The epidemiology of HBV is very similar to that of acquired immune deficiency syndrome, which accounts for why HBV infection is common among patients with AIDS or AIDS related complex. However, HBV is more contagious than HIV.

Both FTC and 3TC exhibit activity against HBV. Furman, et al., "The Anti-Hepatitis B Virus Activities, Cytotoxicities, and Anabolic Profiles of the (−) and (+) Enantiomers of cis-5-Fluoro-1-[2-(Hydroxymethyl)-1,3-Oxathiolane-5-yl] Cytosine" *Antimicrobial Agents and Chemotherapy,* December 1992, page 2686–2692.

A human serum-derived vaccine has been developed to immunize patients against HBV. While it has been found effective, production of the vaccine is troublesome because the supply of human serum from chronic carriers is limited, and the purification procedure is long and expensive. Further, each batch of vaccine prepared from different serum must be tested in chimpanzees to ensure safety. Vaccines have also been produced through genetic engineering. Daily treatments with α-interferon, a genetically engineered protein, has also shown promise.

In light of the fact that acquired immune deficiency syndrome, AIDS-related complex, and hepatitis B virus have reached epidemic levels worldwide, and have tragic effects on the infected patient, there remains a strong need to provide new effective pharmaceutical agents to treat these diseases and that have low toxicity to the host.

Therefore, it is an object of the present invention to provide a method and composition for the treatment of human patients infected with HIV.

It is another object of the present invention to provide a method and composition for the treatment of human patients or other host animals infected with HBV.

SUMMARY OF THE INVENTION

A method and composition for the treatment of HIV and HBV infections in humans and other host animals is disclosed that includes the administration of an effective amount of a [5-carboxamido or 5-fluoro]-2',3'-dideoxy-2', 3'-didehydro-pyrimidine nucleoside or a [5-carboxamido or 5-fluoro]-3'-modified-pyrimidine nucleoside, or a mixture or a pharmaceutically acceptable derivative thereof, including a 5' or $N^4$ alkylated or acylated derivative, or a pharmaceutically acceptable salt thereof, in a pharmaceutically acceptable carrier.

Specifically, compounds of the structure:

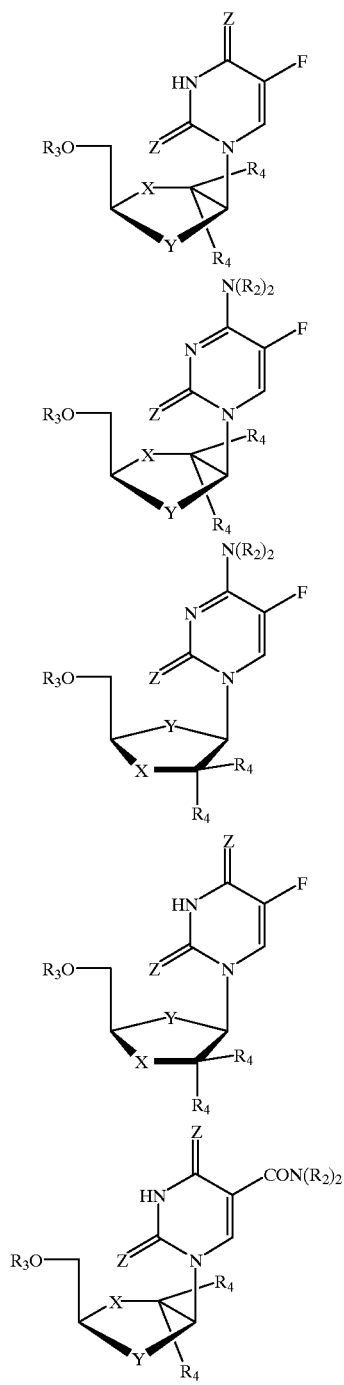

-continued

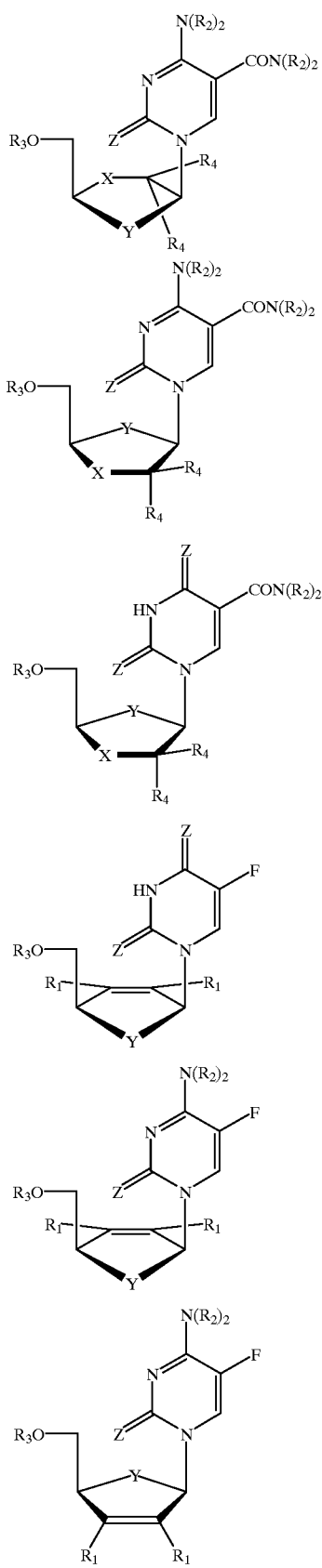

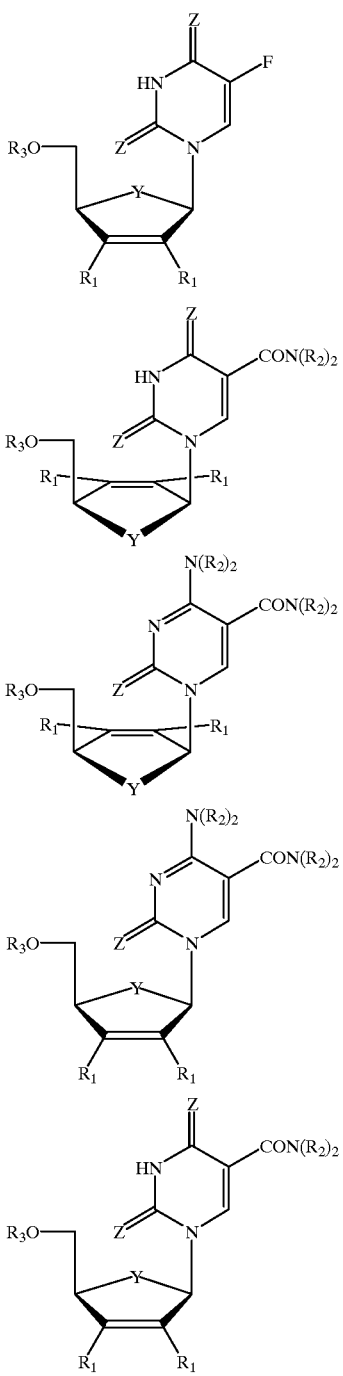

wherein:

X is O, S, $CH_2$, CHF, or $CF_2$;

Y is O, S, $CH_2$, CHF, $CF_2$;

Z is independently O, S or Se;

$R_1$ is independently H or F;

$R_2$ is independently H, OH, $C_1$ to $C_6$ alkyl, or $C(O)(C_1$ to $C_6$ alkyl);

$R_3$ is H, $C(O)(C_1-C_6$ alkyl); alkyl, or mono-, di- or triphosphate; and $R_4$ is independently H, F, Cl, Br, I, OH, $-O(C_1-C_6$alkyl), $-SH$, $-S(C_1-C_6$alkyl); or $-C_1-C_6$alkyl.

In a preferred embodiment for 2',3'-dideoxy-2',3'-didehydro-nucleosides, Y is O or S; Z is O; $R_1$ is H; $R_2$ is H; and $R_3$ is H. In a preferred embodiment for the 3'-modified pyrimidine nucleosides, X is O or S; Y is O; Z is O; $R_1$ is H; $R_2$ is H; $R_3$ is H, and $R_4$ is independently H or F. The term "independently" means that the groups can vary within the compound.

Preferred compounds include the racemic mixture, β-D and β-L isomers of the following compounds: 2-hydroxymethyl-5-(N-5'-carboxamidouracil-1'-yl)-1,3-oxathiolane; 2-hydroxymethyl-4-(N-5'-carboxamidouracil-1'-yl)-1,3-dioxolane; 2-hydroxymethyl-4-(N-5'-fluorocytosin-1'-yl)-1,3-dithiolane; 2-hydroxymethyl-4-(N5'-carboxamidouracil-1'-yl)-1,3-dithiolane; 2-hydroxymethyl-4-(N-5'-fluorocytosin-1-yl)-1,3-oxathiolane; 2-hydroxymethyl-4-(N-5'-carboxamidouracil-1'-yl)-1,3-oxathiolane; 2',3'-dideoxy-2',3'-didehydro-5-fluorocytidine; 2',3'-dideoxy-2',3'-didehydro-5-carboxamidocytidine; 2',3'-dideoxy-5-fluorocytidine; 2',3'-dideoxy-5-carboxamidocytidine; 2',3'-didehydro-2',5-difluorocytidine; 2',3'-dideoxy-2',3'-didehydro-2'-fluoro-5-carboxamidocytidine, 2',3'-dideoxy-2',3'-didehydro-3',5-difluorocytidine; 2',3'-dideoxy-2',3'-didehydro-3'-fluoro-5-carboxamidocytidine; 2',3'-dideoxy-2',3'-didehydro-2',3',5-trifluorocytidine; 2',3'-dideoxy-2',3'-didehydro-2',3'-difluoro-5-carboxamidocytidine; 2',3'-dideoxy-2',3'-didehydro-5-fluorocytidine; 2',3'-dideoxy-2',3'-didehydro-5-carboxamidocytidine; 2',3'-dideoxy-5-fluorocytidine; 2',3'-dideoxy-5-carboxamidocytidine; 2',3'-dideoxy-2',3'-didehydro-2',5-difluorocytidine; 2',3'-dideoxy-2',3'-didehydro-2'-fluoro-5-carboxamidocytidine; 2',3'-dideoxy-2',3'-didehydro-3',5-difluorouridine; 2',3'-dideoxy-2',3'-didehydro-3'-fluoro-5-carboxamidouridine; 2',3'-dideoxy-2',3'-didehydro-2',3',5-trifluorouridine; and 2',3'-dideoxy-2',3'-didehydro-2',3'-difluoro-5-carboxamidouridine.

In another embodiment, the active compound or its derivative or salt can be administered in combination or alternation with another antiviral agent, such as an anti-HIV agent or anti-HBV agent, including those described above. In general, during alternation therapy, an effective dosage of each agent is administered serially, whereas in combination therapy, an effective dosage of two or more agents are administered together. The dosages will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

Nonlimiting examples of antiviral agents that can be used in combination with the compounds disclosed herein include the (-)-enantiomer of 2-hydroxymethyl-5-(5-fluorocytosin-1-yl)-1,3-oxathiolane (FTC); the (-)-enantiomer of 2-hydroxymethyl-5-(cytosin-1-yl)-1,3-oxathiolane (3TC); carbovir, acyclovir, interferon, famciclovir, penciclovir, AZT, DDI, DDC, L-(-)-FMAU, and D4T.

The compounds can also be used to treat equine infectious anemia virus (EIAV), feline immunodeficiency virus, and simian imunodeficiency virus. (Wang, S., Montelaro, R., Schinazi, R. F., Jagerski, B., and Mellors, J. W.: Activity of nucleoside and non-nucleoside reverse transcriptse inhibitors (NNRTI) against equine infectious anemia virus (EIAV). First National Conference on Human Retroviruses and Related Infections, Washington, D.C., Dec. 12–16, 1993; Sellon D. C., Equine Infectious Anemia, Vet. Clin. North Am. Equine Pract. United States, 9: 321–336, 1993; Philpott, H. S., Ebner, J. P., Hoover, E. A., Evaluation of 9-(2-phosphonylmethoxyethyl)adenine therapy for feline immunodeficiency virus using a quantative polymerase chain reaction, Vet. Immunol. Immunopathol. 35:155–166, 1992.)

DETAILED DESCRIPTION OF THE INVENTION

As used herein, the term "enantiomerically enriched nucleoside" refers to a nucleoside composition that includes at least 95% to 98%, or more preferably, 99% to 100%, of a single enantiomer of that nucleoside.

The term $C_1–C_6$ alkyl includes methyl, ethyl, propyl, isopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl.

The invention as disclosed herein is a method and composition for the treatment of HIV and HBV infections, and other viruses replicating in like manner, in humans or other host animals, that includes administering an effective amount of a [5-carboxamido or 5-fluoro]-2',3'-dideoxy-2', 3'-didehydro-pyrimidine nucleoside or [5-carboxamido or 5-fluoro]-3'-modified-pyrimidine nucleoside, a pharmaceutically acceptable derivative, including a 5' or $N^4$ alkylated or acylated derivative, or a pharmaceutically acceptable salt thereof, in a pharmaceutically acceptable carrier. The compounds of this invention either possess antiretroviral activity, such as anti-HIV-1, anti-HIV-2, anti-HBV, and anti-simian immunodeficiency virus (anti-SIV) activity themselves or are metabolized to a compound that exhibits antiretroviral activity.

The disclosed compounds or their pharmaceutically acceptable derivatives or salts or pharmaceutically acceptable formulations containing these compounds are useful in the prevention and treatment of HIV infections and other related conditions such as AIDS-related complex (ARC), persistent generalized lymphadenopathy (PGL), AIDS-related neurological conditions, anti-HIV antibody positive and HIV-positive conditions, Kaposi's sarcoma, thrombocytopenia purpurea and opportunistic infections. In addition, these compounds or formulations can be used prophylactically to prevent or retard the progression of clinical illness in individuals who are anti-HIV antibody or HIV-antigen positive or who have been exposed to HIV.

The compound and its pharmaceutically acceptable derivatives or pharmaceutically acceptable formulations containing the compound or its derivatives are also useful in the prevention and treatment of HBV infections and other related conditions such as anti-HBV antibody positive and HBV-positive conditions, chronic liver inflammation caused by HBV, cirrhosis, acute hepatitis, fulminant hepatitis, chronic persistent hepatitis, and fatigue. These compounds or formulations can also be used prophylactically to prevent or retard the progression of clinical illness in individuals who are anti-HBV antibody or HBV-antigen positive or who have been exposed to HBV.

The compound can be converted into a pharmaceutically acceptable ester by reaction with an appropriate esterifying agent, for example, an acid halide or anhydride. The compound or its pharmaceutically acceptable derivative can be converted into a pharmaceutically acceptable salt thereof in a conventional manner, for example, by treatment with an appropriate base. The ester or salt of the compound can be converted into the parent compound, for example, by hydrolysis.

In summary, the present invention includes the following features:

(a) [5-carboxamido or 5-fluoro]-2',3'-dideoxy-2',3'-didehydro-pyrimidine nucleosides and [5-carboxamido or 5-fluoro]-3'-modified-pyrimidine nucleosides, as outlined above, and pharmaceutically acceptable derivatives and salts thereof;

(b) [5-carboxamido or 5-fluoro]-2',3'-dideoxy-2',3'-didehydro-pyrimidine nucleosides and [5-carboxamido or 5-fluoro]-3'-modified-pyrimidine nucleosides, and pharmaceutically acceptable derivatives and salts thereof for use in medical therapy, for example for the treatment or prophylaxis of a HIV or HBV infection;

(c) use of [5-carboxamido or 5-fluoro]-2',3'-dideoxy-2', 3'-didehydro-pyrimidine nucleosides and [5-carboxamido or 5-fluoro]-3'-modified-pyrimidine nucleosides, and pharmaceutically acceptable derivatives and salts thereof in the manufacture of a medicament for treatment of a HIV or HBV infection;

(d) pharmaceutical formulations comprising [5-carboxamido or 5-fluoro]-2',3'-dideoxy-2',3'-didehydro-pyrimidine nucleosides and [5-carboxamido or 5-fluoro]-3'-modified-pyrimidine nucleosides or a pharmaceutically acceptable derivative or salt thereof together with a pharmaceutically acceptable carrier or diluent; and (e) processes for the preparation of [5-carboxamido or 5-fluoro]-2',3'-dideoxy-2',3'-didehydro-pyrimidine nucleosides and [5-carboxamido or 5-fluoro]-3'-modified-pyrimidine nucleosides, as described in more detail below.

I. Active Compound, and Physiologically Acceptable Derivatives and Salts Thereof The antivirally active compounds disclosed herein are [5-carboxamido or 5-fluoro]-2',3'-dideoxy-2',3'-didehydro-pyrimidine nucleosides and [5-carboxamido or 5-fluoro]-3'-modified-pyrimidine nucleosides, in the racemic or β-D or β-L enantiomerically enriched form.

The active compound can be administered as any derivative that upon administration to the recipient, is capable of providing directly or indirectly, the parent compound, or that exhibits activity itself. Nonlimiting examples are the pharmaceutically acceptable salts (alternatively referred to as "physiologically acceptable salts"), and the 5' and $N^4$ acylated or alkylated derivatives of the active compound (alternatively referred to as "physiologically active derivatives"). In one embodiment, the acyl group is a carboxylic acid ester in which the non-carbonyl moiety of the ester group is selected from straight, branched, or cyclic alkyl, alkoxyalkyl including methoxymethyl, aralkyl including benzyl, aryloxyalkyl such as phenoxymethyl, aryl including phenyl optionally substituted with halogen, $C_1$ to $C_4$ alkyl or $C_1$ to $C_4$ alkoxy, sulfonate esters such as alkyl or aralkyl sulphonyl including methanesulfonyl, the mono, di or triphosphate ester, trityl or monomethoxytrityl, substituted benzyl, trialkylsilyl (e.g. dimethyl-t-butylsilyl) or diphenylmethylsilyl. Aryl groups in the esters optimally comprise a phenyl group. The alkyl group can be straight, branched, or cyclic, and is optimally a $C_1$ to $C_{18}$ group.

Modifications of the active compound, specifically at the $N^4$ and 5'-O positions, can affect the bioavailability and rate of metabolism of the active species, thus providing control over the delivery of the active species. Further, the modifications can affect the antiviral activity of the compound, in some cases increasing the activity over the parent compound. This can easily be assessed by preparing the derivative and testing its antiviral activity according to the methods described herein, or other method known to those skilled in the art.

Since the 1' and 4' carbons of the carbohydrate of the nucleoside (referred to below generically as the sugar moiety) of the nucleosides are chiral, their nonhydrogen substituents (the pyrimidine or purine base and the $CH_2OR$ groups, respectively) can be either cis (on the same side) or trans (on opposite sides) with respect to the sugar ring system. The four optical isomers therefore are represented by the following configurations (when orienting the sugar moiety in a horizontal plane such that the Y substituent is in the back): cis (with both groups "up", which corresponds to the configuration of naturally occurring nucleosides), cis (with both groups "down", which is a nonnaturally occurring configuration), trans (with the C2' substituent "up" and the C4' substituent "down"), and trans (with the C2' substituent "down" and the C4' substituent "up"). The "D-nucleosides" are cis nucleosides in a natural configuration and the "L-nucleosides" are cis nucleosides in the nonnaturally occurring configuration.

As known to those skilled in the art of nucleoside chemistry, in some cases, one of the β-cis enantiomers can be more active, or less toxic, than the other enantiomer. This can be easily determined by separating the enantiomers and testing the activity and cytotoxicity using standard assays.

II. Preparation of the Active Compounds

The nucleosides disclosed herein for the treatment of HIV and HBV infections in a host organism can be prepared according to published methods. β-L-Nucleosides can be prepared from methods disclosed in, or standard modifications of methods disclosed in, for example, the following publications: Jeong, et al., J. of Med. Chem., 36, 182–195, 1993; European Patent Application Publication No. 0 285 884; Génu-Dellac, C., G. Gosselin, A.-M. Aubertin, G. Obert, A. Kirn, and J.-L. Imbach, 3-Substituted thymine α-L-nucleoside derivatives as potential antiviral agents; synthesis and biological evaluation, *Antiviral Chem. Chemother.* 2:83–92 (1991); Johansson, K. N. G., B. G. Lindborg, and R. Noreen, European Patent Application 352 248; Mansuri, M. M., V. Farina, J. E. Starrett, D. A. Benigni, V. Brankovan, and J. C. Martin, Preparation of the geometric isomers of DDC, DDA, D4C and D4T as potential anti-HIV agents, *Bioorg. Med. Chem. Lett.* 1:65–68 (1991); Fujimori, S., N. Iwanami Y. Hashimoto, and K. Shudo, A convenient and stereoselective synthesis of 2'-deoxy-β-L-ribonucleosides, *Nucleosides & Nucleotides* 11:341–349 (1992); Génu-Dellac, C., G. Gosselin, A.-M. Aubertin, G. Obert, A. Kirn, and J.-L. Imbach, 3-Substituted thymine α-L-nucleoside derivatives as potential antiviral agents; synthesis and biological evaluation, *Antiviral Chem. Chemother.* 2:83–92 (1991); Holy, A, Synthesis of 2'-deoxy-L-uridine, *Tetrahedron Lett.* 2:189–192 (1992); Holy, A., Nucleic acid components and their analogs. CLIII. Preparation of 2'-deoxy-L-ribonucleosides of the pyrimidine series. *Collect Czech Chem Commun.* 37:4072–4087 (1992); Holy, A, 2'-deoxy-L-uridine: Total synthesis of a uracil 2'-deoxynucleoside from a sugar 2-aminooxazoline through a 2,2'-anhydronucleoside intermediate. In: Townsend L. B., Tipson R. S., ed. Nucleic Acid Chem. New York: Wiley, 1992: 347–353. vol 1) (1992); Okabe, M., R.-C. Sun, S. Tan, L. Todaro, and D. L. Coffen, Synthesis of the dideoxynucleosides ddC and CNT from glutamic acid, ribonolactone, and pyrimidine bases. *J Org Chem.* 53:4780–4786 (1988); Robins, M. J., T. A. Khwja, and R. K. Robins. Purine nucleosides. XXIX. Synthesis of 21-deoxy-L-adenosine and 21-deoxy-L-guanosine and their alpha anomers. *J Org Chem.* 35:363–639 (1992); Génu-Dellac, C., Gosselin G., Aubertin A.-M., Obert G., Kirn A., and Imbach J.-L., 3'-Substituted thymine α-L-nucleoside derivatives as potential antiviral agents; synthesis and biological evaluation. *Antiviral Chem. Chemother.* 2(2):83–92 (1991); Génu-Dellac, C., Gosselin G., Imbach J.-L.; Synthesis of new 2'-deoxy-3'-substituted-α-L-threo-pentofuranonucleosides of thymine as a potential antiviral agents. *Tet Lett* 32(1):79–82 (1991); Génu-Dellac, C., Gosselin G., Imbach J.-L., Preparation of new acylated derivatives of L-arabinofuranose and 2-deoxy-1-erythro-pentofuranose as precursors for the synthesis of 1-pentofuranosyl nucleosides. 216:240–255 (1991); and Génu-Dellac, C., Gosselin G., Puech F., et al. Systematic synthesis and antiviral evaluation of α-L-arabinofuranosyl and 2'-deoxy-α-L-erythro-pentofuranosyl nucleosides of the five naturally occurring nucleic acid bases. 10(b):1345–1376 (1991).

β-D-Dioxolane-nucleosides can be prepared as disclosed in detail in PCT/US91/09124. The process involves the initial preparation of (2R,4R)- and (2R,4S)-4-acetoxy-2-(protected-oxymethyl)-dioxolane from 1,6-anhydromannose, a sugar that contains all of the necessary stereochemistry for the enantiomerically pure final product, including the correct diastereomeric configuration about the 1 position of the sugar (that becomes the 4'-position in the later formed nucleoside). The (2R,4R)- and (2R,4S)-4-acetoxy-2-(protected-oxymethyl)-dioxolane is condensed with a desired heterocyclic base in the presence of $SnCl_4$, other Lewis acid, or trimethylsilyl triflate in an organic solvent such as dichloroethane, acetonitrile, or methylene chloride, to provide the stereochemically pure dioxolane-nucleoside.

Enzymatic methods for the separation of D and L enantiomers of cis-nucleosides are disclosed in, for example, Nucleosides and Nucleotides, 12(2), 225–236 (1993); European Patent Application Nos. 92304551.2 and 92304552.0 filed by Biochem Pharma, Inc.; and PCT Publication Nos. WO 91/11186, WO 92/14729, and WO 92/14743 filed by Emory University.

Separation of the acylated or alkylated racemic mixture of D and L enantiomers of cis-nucleosides can be accomplished by high performance liquid chromatography with selected chiral stationary phases, as disclosed, for example, in PCT Publication No. WO 92/14729.

Mono, di, and triphosphate derivatives of the active nucleosides can be prepared as described according to published methods. The monophosphate can be prepared according to the procedure of Imai et al., *J. Org. Chem.,* 34(6), 1547–1550 (June 1969). The diphosphate can be prepared according to the procedure of Davisson et al., *J. Org. Chem.,* 52(9), 1794–1801 (1987). The triphosphate can be prepared according to the procedure of Hoard et al., *J. Am. Chem. Soc.,* 87(8), 1785–1788 (1965).

Other references disclosing useful methods that can be used or adapted for the preparation of the active compounds include Hutchinson, D. W. "New Approaches to the Synthesis of Antiviral Nucleosides" *TIBTECH,* 990, 8, 348; Agrofoglio, L. et al. "Synthesis of Carbocyclic Nucleosides" *Tetrahedron,* 1994, 50, 10611; Dueholm, K. L.; Pederson, E. B. *Synthesis,* 1996, 1; Wilson, L. J., Choi, W.-B., Spurling, T., Schinazi, R. F., Cannon, D., Painter, G. R., St.Clair, M., and Furman, P. A. The Synthesis and Anti-HIV Activity of Pyrimidine Dioxanyl Nucleoside Analogues. *Bio. Med. Chem. Lett.,* 1993, 3, 169–174; Hoong, L. K., Strange, L. E., Liotta, D. C., Koszalka, G. W., Burns, C. L., Schinazi, R. F. Enzyme-mediated enantioselective preparation of the antiviral agent 2',3'-dideoxy-5-fluoro-3'-thiacytidine [(−)-FTC] and related compounds. *J. Org. Chem.*, 1992, 57, 5563–5565; Choi, W.-B., Wilson, L. J., Yeola, S., Liotta, D. C., Schinazi, F. R. In situ complexation directs the stereochemistry of N-glycosylation in the synthesis of oxathiolanyl and dioxolanyl nucleoside analogues. *J. Amer. Chem. Soc.*, 1991, 113, 9377–9379; Choi, W.-B., Yeola, S., Liotta, D. C., Schinazi, R. F., Painter, G. R., Davis, M., St.Clair, M., Furman, P. A. The Synthesis, Anti-HIV and Anti-HBV Activity of Pyrimidine Oxathiolane Nucleoside Analogues. *Bio. Med. Chem. Lett.*, 1993, 3, 693–696; Wilson, J. E., Martin, J. L., Borrota-Esoda, K., Hopkins, S. E., Painter, G. R., Liotta, D. C., Furman, P. A. The 5'-Triphosphates of the (−)- and (+)-Enantiomers of Cis-5-Fluoro-1-[2-(hydroxymethyl)-1,3-Oxathioan-5-yl] Cytosine Equally Inhibit Human Immunodeficiency Virus Type-1 Reverse Transcriptase. *Antimicrob. Agents Chemother.*, 1993, 37, 1720–1722.

The following working example provides a method for the preparation of 5-carboxamide-2',3'-dideoxy-3'-thiauridine. Melting points were determined on an Electrothermal IA 8100 digital melting point apparatus and are uncorrected. $^1$H and $^{13}$C NMR spectra were recorded on a General Electric QE-300 (300 MHz) spectrometer; chemical shifts are reported in parts per million (d) and signals are quoted as s (singlet), d (doublet), t (triplet), or m (multiplet). UV spectrum were recorded on Shimadzu UV-2101PC spectrophotometer and FTIR spectra were measured on a Nicolet Impact 400 spectrometer. Mass spectroscopy was performed with JEOL (JMS-SX102/SX102A/E) spectrometer. Experiments were monitored using TLC analysis performed on Kodak chromatogram sheets precoated with silica gel and a fluorescent indicator. Column chromatography, employing silica gel (60–200 mesh; Fisher Scientific, Fair Lawn, N.J.) was used for the purification of products. Tetrakis-(triphenylphosphine)palladium (0) and other chemicals were purchased from Aldrich Chemical Company (Milwaukee, Wis.). Microanalyses were performed at Atlantic Microlab Inc. (Norcross, Ga.). Enzymes were purchased from Amano International Enzyme Co. (Troy, Va.).

EXAMPLE 1

Preparation of 5-carboxamido-2',3'-dideoxy-3-thiauridine

Coupling of 1-O-acetyl-5'-butyryl-3-thiafuranose with 5-iodo-cytidine using tin chloride afforded the protected b-isomer of 5'-butyryl-2',3'-deoxy-5-iodo-3'-thia-cytidine with good stereoselectivity.

To a solution of 5'-butyryl-2',3'-deoxy-5-iodo-3'-thiacytidine (1.63 g; 3.83 mmol) in 100 ml of anhydrous MeOH was added tetrakis-(triphenylphosphine)palladium (0) (0.16 g, 0.14 mmol) and Et$_3$N (0.8 ml). The reaction mixture was maintained under a CO atmosphere for 6 h while heating at 40° C. The solution was concentrated to dryness in vacuo, dissolved in CH$_2$Cl$_2$ then filtered. The resultant precipitate was dissolved in hot CHCl$_3$ to give after crystallization the desired product 5-carboxylic acid methyl ester-2',3'-dideoxy-3'-thiacytidine (0.7 g, 62%) as a white solid. m.p. 217–221° C.; $^1$H NMR (DMSO) d 3.2–3.3 (m, 2H, H-2' and H-2"), 3.75 (s, 3H, OCH$_3$), 3.8–4.0 (m, 2H, H-5' and H-5"), 5.36 (m, 1H, OH-5'), 5.49 (t, 1H, H-4', J$_{4',5'}$=4.0, 6.21 (m, 1H, H-1'), 7.7 and 8.1 (2 br s, 1H each, NH$_2$), 9.0 (s, 1H, H-6); m/z (LSIMS) 288 (M+H)$^+$; Anal. (C$_{10}$H$_{13}$N$_3$O$_5$S) C, H, N, S.

To a solution of 5-carboxylic acid methyl ester-2',3'-dideoxy-3'-thiacytidine (0.2 g, 0.69 mmol) in anhydrous MeOH was added (50 ml) a 2M solution of NH$_3$—MeOH and a catalytic amount of NaCN (20 mg). The resulting solution was stirred at 100 degrees for 20 h and then concentrated in vacuo. The residue was chromatographed on silica gel using CH$_2$Cl$_2$/MeOH (90:10) as eluent to give 5-carboxyamido-2',3'-dideoxy-3'-thiacytidine (0.12 g, 63%) as a white solid. m.p. 190–192 degrees; $^1$H NMR (DMSO) d 3.18 (dd, 1H, H-2' or H-2", J$_{2',2"}$=10.2, J$_{2'\,or\,2",1'}$=1.4), 3.41 (dd, 1H, H-2' or H-2", J$_{2',2"}$=10.1, J$_{2'\,or\,2",1'}$=1.5), 3.8–4.0 (m, 2H , H-5' and H-5"), 5.36 (t, 1H, H-4', J$_{4',5'}$=4.0), 5.5 (br s, 1H, OH-5'), 6.21 (dd, 1H, H-1', J$_{1',2'\,or\,2"}$=4.3, J$_{1',2'\,or\,2"}$=1.9), 7.5 (br s, 2H, NH2), 7.8 and 8.4 (2 br s, 1H each, NH$_2$), 8.6 (s, 1H, H-6); m/z (LSIMS) 273 (M+H)$^+$; Anal. (C$_9$H$_{12}$N$_4$O$_4$S) C, H, N, S.

EXAMPLE 2

Preparation of β-D and β-L enantiomers of 5-carboxylic acid amide-2',3'-dideoxy-3'-thiacytidine 5'-Butyryl-2',3'-deoxy-5-iodo-3'-thiacytidine (3 g, 7 mmol) was dissolved in 900 ml of 4/1 pH 8 buffer/CH$_3$CN. The clear solution was stirred and treated with 1000 units of pig liver esterase (PLE-A, Amano). The progress of the reaction was monitored by HPLC. After 16 hours (50% conversion), the reaction mixture was extracted with 2×600 ml of CHCl$_3$ and 600 ml of EtOAc. The organic extracts were combined, dried over MgSO$_4$, filtered, and concentrated to dryness, and then submitted to the same pathway described in Example 1. The aqueous layer was evaporated to dryness then protected on the 5'-position using butyryl chloride and submitted to the same reaction pathway.

EXAMPLE 3

Preparation of 2',3'-didehydro-2',3'-dideoxy-Pyrimidine Nucleosides

Scheme 1 below provides a general process for the preparation of 2',3'-didehydro-2',3'-dideoxy-pyrimidine nucleosides. This procedure can be adapted for a wide variety of bases, and can be used to provide either the β-D or the β-L isomer, as desired.

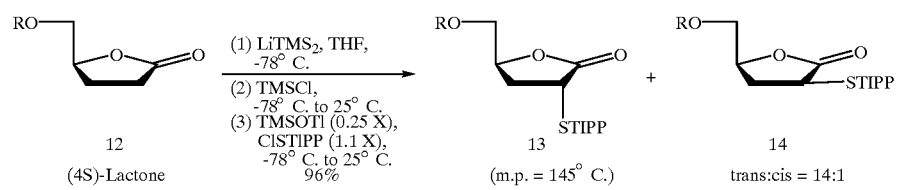

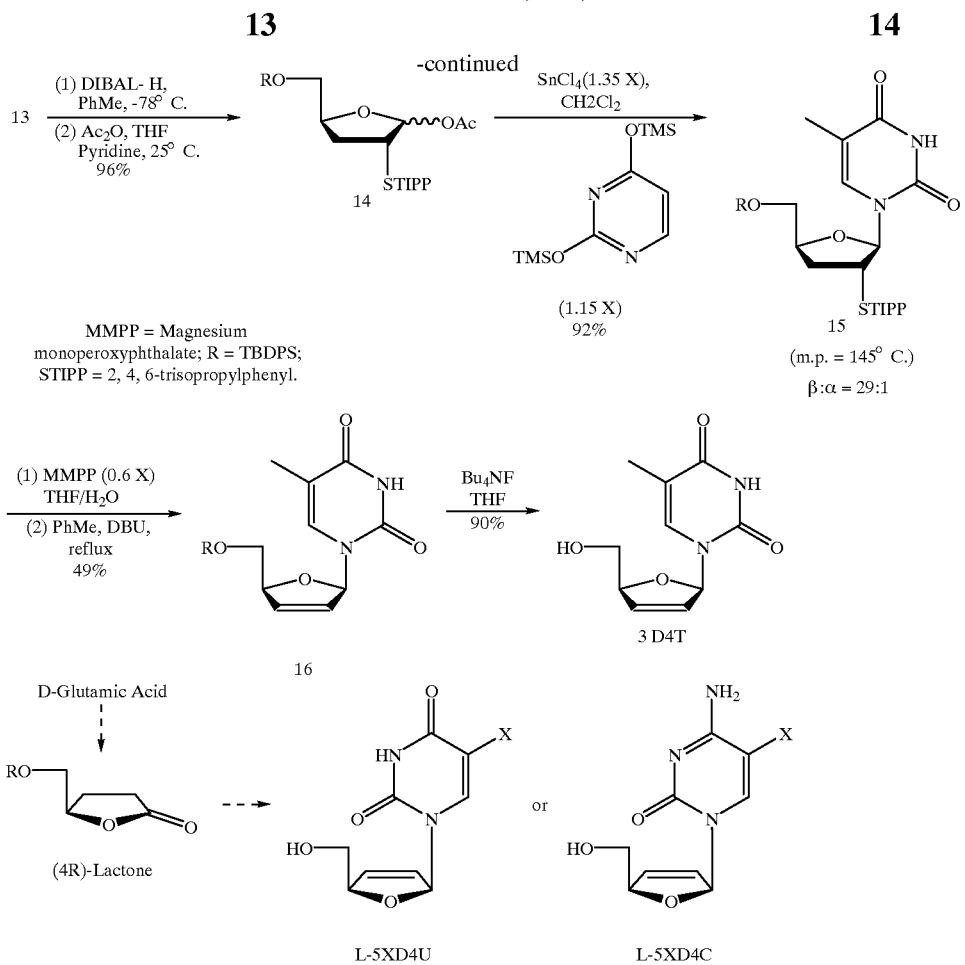

IV. Ability of [5-carboxamido or 5-fluoro]-2',3'-dideoxy-2', 3'-didheydro-pyrimidine nucleoside or [5-carboxamido or 5-fluoro]-3'-modified-pyrimidine nucleosides to Inhibit the Replication of HIV and HBV The ability of nucleosides to inhibit HIV can be measured by various experimental techniques. The technique used herein, and described in detail below, measures the inhibition of viral replication in phytohemagglutinin (PHA) stimulated human peripheral blood mononuclear (PBM) cells infected with HIV-1 (strain LAV). The amount of virus produced is determined by measuring the virus-coded reverse transcriptase enzyme. The amount of enzyme produced is proportional to the amount of virus produced.

EXAMPLE 4

Anti-HIV Activity of 5-Substituted Derivatives of 2',3'-Dideoxy-3'-thiacytidine

A series of 5-substituted derivatives of 2',3'-dideoxy-3-thiacytidine and 2',3'-dideoxy-3'-thiauridine (see Table 1) were synthesized and tested for anti-HIV activity.

Three-day-old phytohemagglutinin-stimulated PBS cells ($10^6$ cells/ml) from hepatitis B and HIV-1 seronegative healthy donors were infected with HIV-1 (strain LAV) at a concentration of about 100 times the 50% tissue culture infectious dose (TICD 50) per ml and cultured in the presence and absence of various concentrations of antiviral compounds.

Approximately one hour after infection, the medium, with the compound to be tested (2 times the final concentration in medium) or without compound, was added to the flasks (5 ml; final volume 10 ml). AZT was used as a positive control.

The cells were exposed to the virus (about $2 \times 10^5$ dpm/ml, as determined by reverse transcriptase assay) and then placed in a $CO_2$ incubator. HIV-1 (strain LAV) was obtained from the Center for Disease Control, Atlanta, Ga. The methods used for culturing the PBH cells, harvesting the virus and determining the reverse transcriptase activity were those described by McDougal et al. (*J. Immun. Meth.* 76, 171–183, 1985) and Spira et al. (*J. Clin. Meth.* 25, 97–99, 1987), except that fungizone was not included in the medium (see Schinazi, et al., *Antimicrob. Agents Chemother.* 32, 1784–1787 (1988); Id., 34:1061–1067 (1990)).

On day 6, the cells and supernatant were transferred to a 15 ml tube and centrifuged at about 900 g for 10 minutes. Five ml of supernatant were removed and the virus was concentrated by centrifugation at 40,000 rpm for 30 minutes (Beckman 70.1 Ti rotor). The solubilized virus pellet was processed for determination of the levels of reverse transcriptase. Results are expressed in dpm/ml of sampled supernatant. Virus from smaller volumes of supernatant (1 ml) can also be concentrated by centrifugation prior to solubilization and determination of reverse transcriptase levels.

The median effective ($EC_{50}$) concentration was determined by the median effect method (*Antimicrob. Agents Chemother.* 30, 491–498 (1986). Briefly, the percent inhibition of virus, as determined from measurements of reverse transcriptase, is plotted versus the micromolar concentration of compound. The $EC_{50}$ is the concentration of compound at which there is a 50% inhibition of viral growth.

Mitogen stimulated uninfected human PBS cells ($3.8 \times 10^5$ cells/ml) were cultured in the presence and absence of drug under similar conditions as those used for the antiviral assay described above. The cells were counted after 6 days using a hemacytometer and the trypan blue exclusion method, as described by Schinazi et al., *Antimicrobial Agents and Chemotherapy*, 22(3), 499 (1982). The $IC_{50}$ is the concentration of compound which inhibits 50% of normal cell growth.

Table 1 provides the $EC_{50}$ values (concentration of nucleoside that inhibits the replication of the virus by 50% in PBM cells, estimated 10% error factor) and $IC_{50}$ values (concentration of nucleoside that inhibits 50% of the growth of mitogen-stimulated uninfected human PBM cells, CEM cells, and in Vero cells) of a number of the tested 5-substituted-3'-thia-2',3'-dideoxypyrimidine nucleosides. In the uracil series none of the derivatives demonstrated any significant antiviral activity. In contrast, in the cytosine series, the racemic 5-acetamide derivative was shown to have antiviral activity with a median effective concentration of 0.77 micromolar and no toxicity up to 100 micromolar in various cell lines. Similar results were obtained on evaluation of the anti-HBV activity. The racemic compound was resolved by an enzyme mediated approach into the β-D and β-L enantiomers, as described in Example 2. Both 5-acetamide derivatives were effective inhibitors of HIV-1 and HBV replication.

greater than 3.5-fold (for HBV virion DNA) or 3.0-fold (for HBV DNA replication intermediates) from the average levels for these HBV DNA forms in untreated cells are considered to be statistically significant [P<0.05]. The levels of integrated HBV DNA in each cellular DNA preparation (which remain constant on a per cell basis in these experiments) were used to calculate the levels of intracellular HBV DNA forms, thereby ensuring that equal amounts of cellular DNA were compared between separate samples.

Typical values for extracellular HBV virion DNA in untreated cells ranged from 50 to 150 pg/ml culture medium (average of approximately 76 pg/ml). Intracellular HBV DNA replication intermediates in untreated cells ranged from 50 to 100 pg/μg cell DNA (average approximately 74 pg/μg cell DNA). In general, depressions in the levels of intracellular HBV DNA due to treatment with antiviral compounds are less pronounced, and occur more slowly, than depressions in the levels of HBV virion DNA (Korba and Milman, 1991, *Antiviral Res.*, 15:217).

The manner in which the hybridization analyses were performed for these experiments resulted in an equivalence of approximately 1.0 pg of intracellular HBV DNA to 2–3 genomic copies per cell and 1.0 pg/ml of extracellular HBV DNA to $3 \times 10^5$ viral particles/ml.

Toxicity analyses were performed to assess whether any observed antiviral effects were due to a general effect on cell

TABLE 1

Biological Evaluation of Various 5-Substituted-3'-thia-2',3'-dideoxypyrimidine Nucleosides Against HIV-1$_{LAI}$, HSV-1$_F$, and for Cytotoxicity in PBM, CEM, and Vero Cells

| Base | 5-Substituent | Configuration | Anti-HIV-1 in PBMC $EC_{50}$, μM | Toxicity in PBM cells $IC_{50}$, μM | Toxicity in CEM cells $IC_{50}$, μM | Toxicity in Vero cells $IC_{50}$, μM | Anti-HSV-1 in Vero cells $EC_{50}$, μM[a] |
|---|---|---|---|---|---|---|---|
| U | Nitro | (±)-β-DL | 122.2 | >100 | >100 | >100 | |
| C | Nitro | (±)-β-DL | 100.0 | >100 | >100 | >100 | |
| U | Amino | (±)-β-DL | 118.6 | >100 | >100 | >100 | |
| C | Amino | (±)-β-DL | 26.4 | >100 | >100 | >100 | |
| U | Ethynyl | (±)-β-DL | 23.8 | >100 | >100 | >100 | |
| C | Ethynyl | (±)-β-DL | >100 | >100 | >100 | >100 | |
| U | Ethyl | (±)-β-DL | >100 | >100 | >100 | >100 | |
| C | Ethyl | (±)-β-DL | 102.5 | >100 | >100 | >100 | |
| U | Cyano | (±)-β-DL | >100 | >100 | >100 | ND | |
| C | Cyano | (±)-β-DL | >100 | >100 | >100 | >100 | |
| U | Methoxycarbonyl | (±)-β-DL | >100 | >100 | >100 | >100 | >100 |
| C | Methoxycarbonyl | (±)-β-DL | 38.9 | >100 | >100 | >100 | |
| U | Carboxamide | (±)-β-DL | >100 | >100 | >100 | >100 | |
| C | Carboxamide | (±)-β-DL | 0.77 | >100 | >100 | >100 | >100 |
| C | Carboxamide | (+)-β-D | 8.5 | >100 | >100 | >100 | |
| C | Carboxamide[b] | (−)-β-L | 3.6 | >100 | >100 | >100 | |
| C | N-Methylaminoformyl | (±)-β-DL | >100 | >100 | >100 | >100 | |
| C | N,N-Dimethylaminoformyl | (±)-β-DL | >100 | >100 | >100 | >100 | |
| C | H (3TC) | (−)-β-L | 0.002 | >100 | >100 | >100 | >100 |

[a]Acyclovir used as apositive control had an $EC_{50}$ of 0.04 μM.
[b]$EC_{50}$ against HIV-2$_{ROD2}$ and SIV$_{SMM}$ was 1.6 and 4.0 μM, respectively.

EXAMPLE 5

Anti-HIV Activity of 5-Substituted Derivatives of 2',3'-Dideoxy-3'-thiacytidine

The ability of the active compounds to inhibit the growth of virus in 2.2.15 cell cultures (HepG2 cells transformed with hepatitis virion) can be evaluated as described in detail below.

A summary and description of the assay for antiviral effects in this culture system and the analysis of HBV DNA has been described (Korba and Milman, 1991, *Antiviral Res.*, 15:217). The antiviral evaluations were performed on two separate passages of cells. All wells, in all plates, were seeded at the same density and at the same time.

Due to the inherent variations in the levels of both intracellular and extracellular HBV DNA, only depressions viability. The method used herein was the measurement of the uptake of neutral red dye, a standard and widely used assay for cell viability in a variety of virus-host systems, including HSV and HIV. Toxicity analyses were performed in 96-well flat bottomed tissue culture plates. Cells for the toxicity analyses were cultured and treated with test compounds with the same schedule as described for the antiviral evaluations below. Each compound was tested at 4 concentrations, each in triplicate cultures (wells "A", "B", and "C"). Uptake of neutral red dye was used to determine the relative level of toxicity. The absorbance of internalized dye at 510 nm ($A_{sin}$) was used for the quantitative analysis. Values are presented as a percentage of the average $A_{sin}$ values in 9 separate cultures of untreated cells maintained on the same 96-well plate as the test compounds. Dye uptake in the 9 control cultures on plate 5 ranged from 91.6% to 110.4%, and on plate 6 from 96.6% to 109%.

The results of the HBV assay are provided in Table 2. As indicated, the β-D and β-L enantiomers of 5-carboxylic acid amide-2',3'-dideoxy-3'-thiacytidine (referred to as β-L- and β-D-carboxamide) exhibit significant activity against HBV and are relatively nontoxic.

TABLE 2

EFFECT OF 5-CARBOXAMIDE DERIVATIVES OF 3TC AGAINST HEPATITIS B VIRUS IN TRANSFECTED HEPG-2 (2.2.15) CELLS ON DAY 9

| Compound | HBV virion[a] | | HBV RI[b] | | Cytotoxicity | Selectivity Index $IC_{50}/EC_{90}$ | |
|---|---|---|---|---|---|---|---|
| | $EC_{50} \pm SD^c$ | $EC_{90} \pm SD^c$ | $EC_{50} \pm SD^c$ | $EC_{90} \pm SD^c$ | $IC_{50} \pm SD^c$ | Virion | RI |
| β-D-DDC | 1.4 ± 0.2 | 9.6 ± 1.1 | 3.4 ± 0.4 | 13.0 ± 1.4 | 236 ± 21 | 26 | 18 |
| β-L-carboxamide | 0.29 ± 0.02 | 1.5 ± 0.2 | 1.3 ± 0.1 | 9.9 ± 0.8 | 1747 ± 212 | 1165 | 177 |
| β-D-carboxamide | 0.11 ± 0.012 | 0.9 ± 0.1 | 0.5 ± 0.04 | 3.8 ± 0.3 | 1124 ± 72 | 1249 | 296 |
| β-L-FTC | 0.04 ± 0.006 | 1.1 ± 0.1 | 0.16 ± 0.01 | 0.39 ± 0.22 | 746 ± 33 | 678 | 1,913 |

[a]Extracellular DNA; untreated control had 102 pg/ml
[b]Replicative intermediates (Intracellular DNA), untreated control had 87 pg/μg cell DNA
[c]μM

EXAMPLE 5

Anti-HIV Activity of 2',3'-Didehydro-2',3'-dideoxy-pyrimidine nucleosides

Table 3 provides the $EC_{50}$ values (concentration of nucleoside that inhibits the replication of the HIV-1 and HIV-2 by 50% in PBM cells, estimated 10% error factor) and $IC_{50}$ values (concentration of nucleoside that inhibits 50% of the growth of mitogen-stimulated uninfected human PBM cells, CEM cells, and in Vero cells) of β-L-2',3'-didehydro-2',3'-dideoxy-cytidine and β-L-2',3'-didehydro-2',3'-dideoxy-5-fluoro-cytidine. As indicated, both compounds exhibit significant activity against HIV, and are relatively nontoxic.

EXAMPLE 5

Anti-HIV Activity of 2',3'-Didehydro-2',3'-dideoxy-pyrimidine nucleosides

TABLE 3

Biological Evaluation of Various β-L-2',3'-dideoxypyrimidine nucleosides Against HIV-1$_{LAI}$, HIV-2$_{ROD2}$, SIV$_{SMM}$, and for Cytotoxicity in PBM, CEM, and Vero Cells

| Compound | Configuration | Anti-HIV-1 in PBMC $EC_{50}, \mu M$ | Anti-HIV-2 in PBMC $EC_{50}, \mu M$ | Anti-SIV in PBMC $EC_{50}, \mu M$ | Toxicity in PBM cells $IC_{50}, \mu M$ | Toxicity in CEM cells $IC_{50}, \mu M$ | Toxicity in Vero cells $IC_{50}, \mu M$ |
|---|---|---|---|---|---|---|---|
| L-D4C | (−)-β-L | 0.0058 | 0.033 | 0.048 | >100 | 0.73 | 10.8 |
| L-F-D4C | (−)-β-L | 0.0015 | 0.0006 | 0.00015 | >100 | 7.3 | 40.3 |
| 3TC | (−)-β-L | 0.002 | 0.020 | 0.02 | >100 | >100 | >100 |

TABLE 4

Effect of DDC Derivatives Against Hepatitis B Virus (HBV) in Transfected HEpG-2 (2.2.15) Cells on Day 9

| Compound | HBV virion[a] | | HBV RI[b] | | Cytotoxicity | Selectivity Index $IC_{50}/EC_{90}$ | |
|---|---|---|---|---|---|---|---|
| | $EC_{50} \pm SD^c$ | $EC_{90} \pm SD^c$ | $EC_{50} \pm SD^c$ | $EC_{90} \pm SD^c$ | $IC_{50} \pm SD^c$ | Virion | RI |
| β-D-DDC | 1.5 ± 0.2 | 8.2 ± 0.8 | 2.4 ± 0.3 | 12.0 ± 1.1 | 259 ± 18 | 37 | 22 |
| β-L-D4C | 0.15 ± 0.02 | 0.33 ± 0.04 | 0.91 ± 0.09 | 2.3 ± 0.3 | 1044 ± 92 | 1149 | 454 |
| β-L-F-D4C | 0.28 ± 0.03 | 0.41 ± 0.04 | 0.33 ± 0.04 | 0.75 ± 0.07 | >3 | >7.3 | >4 |

[a]Extracellular DNA; untreated control had 88 pg/ml
[b]Replicative intermediates (Intracellular DNA), untreated control had 79 pg/μg cell DNA
[c]μM III. Preparation of Pharmaceutical Compositions Humans suffering from diseases caused by HIV or HBV infection can be treated by administering to the patient an effective amount of a [5-carboxamido or 5-fluoro]-2',3'-dideoxy-2',3'-didehydro-pyrimidine nucleoside or [5-carboxamido or 5-fluoro]-3'-modified-pyrimidine nucleoside or a pharmaceutically acceptable derivative or salt thereof in the presence of a pharmaceutically acceptable carrier or diluent. The active materials can be administered by any appropriate route, for example, orally, parenterally, intravenously, intradermally, subcutaneously, or topically, in liquid or solid form.

The active compound is included in the pharmaceutically acceptable carrier or diluent in an amount sufficient to deliver to a patient a therapeutically effective amount of compound to inhibit viral replication in vivo, especially HIV and HBV replication, without causing serious toxic effects in the patient treated. By "inhibitory amount" is meant an amount of active ingredient sufficient to exert an inhibitory effect as measured by, for example, an assay such as the ones described herein.

A preferred dose of the compound for all of the above-mentioned conditions will be in the range from about 1 to 50 mg/kg, preferably 1 to 20 mg/kg, of body weight per day, more generally 0.1 to about 100 mg per kilogram body weight of the recipient per day. The effective dosage range of the pharmaceutically acceptable derivatives can be calculated based on the weight of the parent nucleoside to be delivered. If the derivative exhibits activity in itself, the effective dosage can be estimated as above using the weight of the derivative, or by other means known to those skilled in the art.

The compound is conveniently administered in unit any suitable dosage form, including but not limited to one containing 7 to 3000 mg, preferably 70 to 1400 mg of active ingredient per unit dosage form. A oral dosage of 50–1000 mg is usually convenient.

Ideally the active ingredient should be administered to achieve peak plasma concentrations of the active compound of from about 0.2 to 70 $\mu$M, preferably about 1.0 to 10 $\mu$M. This may be achieved, for example, by the intravenous injection of a 0.1 to 5% solution of the active ingredient, optionally in saline, or administered as a bolus of the active ingredient.

The concentration of active compound in the drug composition will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

A preferred mode of administration of the active compound is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The compound can be administered as a component of an elixir, suspension, syrup, wafer, chewing gum or the like. A syrup may contain, in addition to the active compounds, sucrose as a sweetening agent and certain preservatives, dyes and colorings and flavors.

The compound or a pharmaceutically acceptable derivative or salts thereof can also be mixed with other active materials that do not impair the desired action, or with materials that supplement the desired action, such as antibiotics, antifungals, antiinflammatories, or other antivirals, including other nucleoside anti-HIV compounds. Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In a preferred embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation.

Liposomal suspensions (including liposomes targeted to infected cells with monoclonal antibodies to viral antigens) are also preferred as pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its monophosphate, diphosphate, and/or triphosphate derivatives is then introduced into the container. The container is then swirled by hand to free lipid material from the sides of the container and to disperse lipid aggregates, thereby forming the liposomal suspension.

This invention has been described with reference to its preferred embodiments. Variations and modifications of the invention, will be obvious to those skilled in the art from the foregoing detailed description of the invention. It is intended that all of these variations and modifications be included within the scope of the appended claims.

We claim:

1. A composition comprising an effective HIV or HBV treatment amount of a $\beta$-D-nucleoside of the formula:

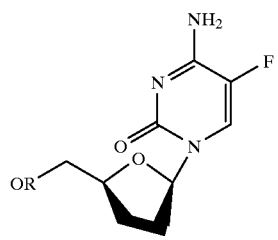

wherein R is hydrogen acyl, monophosphate, diphosphate, or triphosphate; in combination or alternation with a second compound selected from the group consisting of 2-hydroxymethyl-5-(5-fluorocytosin-1-yl)-1,3-oxathiolane, 2-hydroxymethyl-5-(cytosin-1-yl)-1,3-oxathiolane, 9-(4-hydroxymethyl)-2-cyclopenten-1-yl)-guanine (carbovir), 9-((2-hydroxyethoxy)methyl)-guanine (acyclovir), interferon, 3'-deoxy-3'-azidothymidine (AZT), 2',3'-dideoxyinosine (DDI), 2',3'-dideoxycytidine (DDC), (−)-2'-fluoro-5-methyl-β-L-arabinofuranosyluridine (L-(−)-FMAU), and 2',3'-didehydro-2',3'-dideoxythymidine (D4T).

2. The composition of claim 1, wherein R is hydrogen.
3. The composition of claim 1, wherein R is monophosphate.
4. The composition of claim 1, wherein R is selected from the group consisting of diphosphate and triphosphate.
5. The composition of claim 1, wherein R is diphosphate.
6. The composition of claim 1, wherein the second compound is 2-hydroxymethyl-5-(5-fluorocytosin-1-yl)-1,3-oxathiolane.
7. The composition of claim 1, wherein the second compound is 2-hydroxymethyl-5-(cytosin-1-yl)-1,3-oxathiolane.
8. The composition of claim 1, wherein the second compound is carbovir.
9. The composition of claim 1, wherein the second compound is acyclovir.
10. The composition of claim 1, wherein the second compound is interferon.
11. The composition of claim 1, wherein the second compound is AZT.
12. The composition of claim 1, wherein the second compound is DDI.
13. The composition of claim 1, wherein the second compound is DDC.
14. The composition of claim 1, wherein the second compound is L-(−)-FMAU.
15. The composition of claim 1, wherein the second compound is D4T.
16. The composition of claim 1, wherein the combination is effective against HIV.
17. The composition of claim 1, where the alternation is effective against HIV.
18. The composition of claim 1, wherein the combination is effective against HBV.
19. The composition of claim 1, wherein the alternation is effective against HBV.

* * * * *

UNITED STATES PATENT AND TRADEMARK OFFICE
CERTIFICATE OF CORRECTION

PATENT NO. : 5,905,070
DATED : May 18, 1999
INVENTOR(S) : Raymond F. Schinazi and Dennis C. Liotta It is certified that error appears in the above-identified patent and that said Letters Patent is hereby corrected as shown below:

Title page, Item [54] and Column 1, line 1,
Title, "[5-CABOXAMIDO" should read -- [5-CARBOXAMIDO --.

Column 21,
Line 1, the formula is incorrect, and should read:

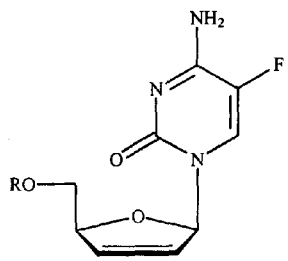

Line 9, a comma should be placed after the term "hydrogen" and before the term "acyl".

Signed and Sealed this

Twentieth Day of April, 2004

JON W. DUDAS
*Acting Director of the United States Patent and Trademark Office*